(12) United States Patent
Vanlandeghem et al.

(10) Patent No.: US 9,638,555 B2
(45) Date of Patent: May 2, 2017

(54) METHOD TO DETERMINE OR MONITOR THE AMOUNT OR THE DISTRIBUTION OF ADDITIONAL MATERIAL PRESENT IN A FLOW OF A FLOWABLE SUBSTANCE

(71) Applicant: NV BEKAERT SA, Zwevegem (BE)

(72) Inventors: Bart Vanlandeghem, Ghent (BE); Johan De Pontieu, Harelbeke (BE); Gerhard Vitt, Pfungstadt (DE); Ann Lambrechts, Avelgem (BE)

(73) Assignee: NV BEKAERT SA, Zwevegem (BE)

( * ) Notice: Subject to any disclaimer, the term of this patent is extended or adjusted under 35 U.S.C. 154(b) by 82 days.

(21) Appl. No.: 14/441,615

(22) PCT Filed: Nov. 20, 2013

(86) PCT No.: PCT/EP2013/074225
§ 371 (c)(1),
(2) Date: May 8, 2015

(87) PCT Pub. No.: WO2014/079853
PCT Pub. Date: May 30, 2014

(65) Prior Publication Data
US 2015/0292923 A1    Oct. 15, 2015

(30) Foreign Application Priority Data

Nov. 21, 2012 (EP) .................................... 12193528

(51) Int. Cl.
*G01F 1/74*   (2006.01)
*G01F 1/58*   (2006.01)
(Continued)

(52) U.S. Cl.
CPC ................. *G01F 1/58* (2013.01); *G01F 1/74* (2013.01); *G01F 9/00* (2013.01); *G01N 27/72* (2013.01)

(58) Field of Classification Search
None
See application file for complete search history.

(56) References Cited

U.S. PATENT DOCUMENTS 5,257,530 A    11/1993   Beattie et al.
5,467,650 A *  11/1995   Cushing .................. G01F 1/002
                                                            702/45
(Continued)

FOREIGN PATENT DOCUMENTS

JP         2001-281034 A      10/2001

*Primary Examiner* — Harshad R Patel
(74) *Attorney, Agent, or Firm* — Foley & Lardner LLP (57) ABSTRACT

A method includes the steps of (a) providing a flow of a flowable substance, the flow comprising bulk material and additional material; (b) determining the volume flow of the flow of the flowable substance at one or more detection points X along the flow of the flowable substance; (c) determining a signal caused by the additional material present in the flow of the flowable substance at one or more detection points Y along the flow of the flowable substance, the signal being proportional to the amount of the additional material present in the flow of the flowable substance passing the one or more detection points Y; and (d) converting the signal caused by the additional material present in the flow of the flowable substance into a signal per unit of volume of the flow of the flowable substance.

12 Claims, 3 Drawing Sheets

(51) Int. Cl.
*G01F 9/00* (2006.01)
*G01N 27/72* (2006.01)

(56) References Cited

U.S. PATENT DOCUMENTS

| | | | |
|---|---|---|---|
| 5,741,979 A * | 4/1998 | Arndt | G01F 1/74 |
| | | | 324/639 |
| 2007/0044572 A1 | 3/2007 | Davis et al. | |
| 2009/0148857 A1* | 6/2009 | Srivastava | B01L 3/502761 |
| | | | 435/7.1 |
| 2009/0231149 A1 | 9/2009 | Angell et al. | |
| 2010/0223976 A1* | 9/2010 | Jakubenas | G01F 1/7042 |
| | | | 73/1.16 |

* cited by examiner

METHOD TO DETERMINE OR MONITOR THE AMOUNT OR THE DISTRIBUTION OF ADDITIONAL MATERIAL PRESENT IN A FLOW OF A FLOWABLE SUBSTANCE

TECHNICAL FIELD

The invention relates to a method to determine or monitor the amount or the distribution of additional material present in a flow of a flowable substance. The method according to the present invention is in particular suitable to determine or monitor the amount or distribution of additional material present in a flow of concrete or mortar, for example during unloading of the flow of concrete or mortar.

The invention further relates to an apparatus to determine or monitor the amount or the distribution of additional material present in a flow of a flowable substance.

BACKGROUND ART

For many applications it is important to control the amount of material that is present in a flow of a flowable substance. For other applications it is important to control the distribution of material added with a flow of a flowable substance. For still other applications it is important to control both the amount of material that is added with a flow of a flowable substance and the distribution of material added with the flow of a flowable substance. To control the amount of material added and/or to control the distribution of material added, it is important to measure or monitor the volume flow of a flowable substance.

For steel fibre reinforced concrete it is extremely important to control the amount of reinforcing fibres added to the concrete and/or to control the distribution of the reinforcing fibres over the concrete volume. Control of the amount and/or the distribution of steel reinforcing fibres added to the concrete is for example important to guarantee a correct reinforcement. Especially for structural applications strict process control and/or quality control is important.

At present it is difficult to control the amount of fibres added to fibre reinforced concrete once the reinforcing fibres are in the concrete, fresh or hardened. Today process and quality control is done by wash-out tests. In wash-out tests at regular intervals during the unloading of the concrete samples of concrete are taken from the truck mixer. As wash-out tests require sampling, weighing, washing out and counting or weighing of the steel fibres, these tests are time consuming and labour intensive. Furthermore these tests have the disadvantage that they require special equipment and might deliver results too late.

There are instruments available on the market to determine the amount of steel fibre present in a cube of concrete (fresh or hardened) by inductive measurements. A drawback of this technology is the required calibration. Furthermore this technology does not allow on-line measurement. The samples need to be filled completely with concrete and three measurements are required along the three main axes to determine the amount of steel fibres present.

Therefore it is clear that there is an urgent need for control mechanisms to measure or monitor the amount and/or distribution of steel reinforcing fibres during the unloading of the steel fibre reinforced concrete.

DISCLOSURE OF INVENTION

It is an object of the present invention to provide a method to determine or monitor the amount of additional material present in a flow of a flowable substance or to determine or monitor the distribution of additional material present in a flow of a flowable substance, in particular during unloading of this flow.

It is another object of the present invention to provide a non-destructive method to determine the amount or the distribution of additional material present in a flow of a flowable substance.

It is a further object to provide a method to determine the amount or the distribution of additional material present in a flow of a flowable substance not requiring wash-out tests.

It is a further object to provide a method to determine the amount or the distribution of additional material present in a flow of a flowable substance that is suitable for a flow passing through a closed flow channel as well as for a flow passing through an open flow channel, for example through a chute of a mixing truck.

It is still a further object to provide a method that is suitable to determine or monitor the amount or distribution of additional material present in a constant or continuous flow of a flowable substance as well as in a non-constant or non-continuous flow of a flowable substance. The method according to the present is furthermore suitable for a homogeneous flow as well as for a non-homogeneous flow, for a flow having a constant height and/or a constant cross-section as well as for a flow having a variable height and/or a variable cross-section.

It is a further object to provide a method that is suitable to determine or monitor the amount or the distribution of steel fibres present in a flow of concrete during unloading of said flow of concrete.

It is a further object of the present invention to provide an apparatus to apparatus to determine or monitor the amount or distribution of additional material present in a flow of a flowable substance.

It is still a further object to provide an apparatus to determine or monitor the amount or distribution of steel fibres in a flow of concrete during unloading of said flow of concrete.

According to a first aspect of the present invention, a method to determine or monitor the amount or the distribution of additional material present in a flow of a flowable substance is provided.

The method comprises the steps of providing a flow of a flowable substance; said flow of said flowable substance comprising bulk material and additional material;

determining the volume flow of said flow of said flowable substance at one or more detection points X along said flow of said flowable substance;

determining a signal caused by said additional material present in said flow of said flowable substance at one or more detection points Y along said flow of said flowable substance, said signal being proportional to the amount of said additional material present in said flow of said flowable substance passing said one or more detection points Y;

converting said signal caused by said additional material present in said flow of said flowable substance in a signal per unit of volume of said flow of said flowable substance.

The volume flow can be determined at one or more detection points X located at any position along the flow of the flowable substance, for example at a position located below, above or around the flow of the flowable substance.

The volume flow can be determined at one detection point, called detection point $X_1$ or the volume flow can be determined at n detection points X, called detection points $X_1, \ldots X_n$; with n equal or larger than 2, for example equal to 3, 4, 5, 6 or 10.

The signal caused by the additional material present in the flow of the flowable substance can be determined at one or more detection points Y located at any position along the flow of the flowable substance, for example at a position located below, above or around the flow of the flowable substance.

The signal caused by the additional material present in the flow of the flowable substance can be determined at one detection point, called detection point $Y_1$ or the signal can be determined at a number of detection points $Y_1, \ldots, Y_n$; with n equal or larger than 2, for example equal to 3, 4, 5, 6 or 10.

The volume flow and the signal caused by the flow of the flowable substance can be determined at the same location or at different locations, at the same detection point or points or at different detection point or points.

According to a preferred method of the present invention the method according to the present invention comprises additionally the following step proportioning backwards said signal per unit of volume of said flow of said flowable substance to determine or monitor the amount of said additional material present in said flow of said flowable substance or to determine or monitor the distribution of said additional material present in said flow of said flowable substance per unit of volume of said flow of said flowable substance.

The amount of additional material present in the flow of the flowable substrate can be expressed in function of a partial volume of the flow or in function of the total volume of the flow.

For the purpose of this invention with "flow of a flowable substance" is meant any substance moving in one direction.

With "flowable substance" is meant any substance that is able to flow such as slurries, liquids, plastics or free flowing powders.

The flowable substance preferably comprises bulk material and additional material. As bulk material any material that is able to flow can be considered. Preferred examples of bulk material comprise concrete or mortar.

Other preferred examples of bulk material comprise magnetic material, for example ferromagnetic material.

Preferred additional materials comprise magnetic material. The magnetic material comprises for example ferromagnetic material.

As ferromagnetic material any material that is ferromagnetic can be considered.

Examples of ferromagnetic material comprise ferromagnetic aggregates, metal particles, metal components or particles or components comprising metal.

Preferably, the ferromagnetic material comprises metal compounds, such as metal fibres. The metal compounds are preferable steel compounds such as steel fibres.

In preferred embodiments the flowable substance comprises a non magnetic or non-ferromagnetic bulk material and magnetic or more particularly ferromagnetic additional material. An example of a preferred flowable substance comprises concrete as bulk material and metal fibres, in particular steel fibres as additional material.

Steel fibres are for example steel fibres known under the trademark Dramix®.

The steel fibres can for example be straight. Alternatively, the steel fibres are non-straight as for examples fibres having a middle portion provided with hook-shaped ends at one or both sides of this middle portion, corrugated fibres or fibres having a cross-section that is varying along the length of the fibre.

For steel fibres, the thickness or diameter preferably varies from 0.15 mm to 1.3 mm. The thickness of diameter is for example equal to 0.5 mm, 0.55 mm, 0.6 mm, 0.65 mm, 0.7 mm, 0.75 mm, 0.8 mm. The length-to-diameter ratio for steel fibres is, for practical and economical reasons, mostly situated between 10 and 200 and preferably minimally amounts to 40. The length-to-diameter ratio is for example equal to 45, 60 or 80. For non-straight fibres, the length is the rectilinear distance between the ends of the fibres, whereas the diameter of fibres of which the diameter varies along the length is defined as the average diameter over the entire length. The length is for example equal to 35 mm, 40 mm, 45 mm, 50 mm, 55 mm, 60 mm, 65 mm, 80 mm or 100 mm.

The volume flow Q is defined as the volume passing through a section per unit of time.

The volume flow Q can be calculated by using the formula:

$$Q = v \cdot A$$

With v: the speed or velocity of the flow of the flowable substance;

A: the cross-sectional area

The volume flow can be calculated by determining the velocity of the flow of the flowable substance and the cross-sectional area. The velocity of the flow of the flowable substance is for example determined at one detection point or at a number n of detection points with n being equal or higher than 2, for example equal to 3, 4, 5, 6, 10 or even higher than 10.

The n detection points can be positioned along the flow of the flowable substance, for example at a position located below, above or around the flow of the flowable substance. In a preferred embodiment, the n detection points are positioned along one cross-section of the flow. This is in particular advantageous in case of a non-uniform speed distribution within the considered cross-section.

In some cases it can be preferred or even required to correct the measured volume flow Q for example because the cross-sectional area A is not constant, because the height or height profile of the flow is not constant, because the width or width profile of the flow is not constant, because the flow rate is not constant over the height and/or width of the flow, because of friction between the flow of the flowable substance and the flow channel, . . . .

The cross-sectional area can be determined by determining the cross-section of the flow of the flowable substance, by determining the height or the height profile of the flow of the flowable substance, by determining the width or the width profile of the flow of the flowable substance or by determining the height and the width or the height and the width profile of the flow of the flowable substance.

It is important to notice that the method according to the present invention is suitable for a flow of a flowable substance having a constant height during the flowing as well as for a flow of a flowable substance having a variable height during the flowing. Furthermore, the method according to the present invention is suitable for a flow of a flowable substance flowing through a flow channel having a constant cross-section or flowing through a flow channel having a variable cross-section.

The method according to the present invention is suitable for a homogeneous flow or an inhomogeneous, for a flow having a constant amount of additional material per unit of volume as well as for a flow having a variable amount of additional material per unit of volume. Furthermore, the method according to the present invention is suitable for a constant or continuous flow as well as for a non-constant or non-continuous flow, for example an interrupted flow.

The velocity of a flow of a flowable substance can for example be determined by using any known method.

The measurement of the velocity of the flow of the flowable substance can be done by using ultrasonic sensors, by visible inspection or by measuring or monitoring a signal caused by the flow of the flowable substance, for example a signal caused by the bulk material or caused by the additional material added to the bulk material. The method can be a method requiring contact with the flow of the flowable substance. Alternatively, the method can be a non-contacting method.

The signal caused by the additional material present in the flow of the flowable substance is proportional to the amount of additional material present in the flow of the flowable substance or proportional to the distribution of the additional material present in the flow of the flowable substance.

The signal that is determined is for example proportional to the density, the electrical conductivity, the thermal conductivity, the inductance or the magnetic properties of additional material present in the flow of the flowable substance, more particularly to the density, the electrical conductivity, the thermal conductivity, the inductance or the magnetic properties of the additional material present in the flow of the flowable substrate Depending on the type of signal to be detected the most appropriate detector has to be chosen.

The signal that is determined is for example proportional to the amount of magnetic compounds or more particularly to the amount of ferromagnetic compounds present in the flow of the flowable substance, such as the amount of steel fibres.

Alternatively, the property that is determined is proportional to the distribution of the additional material present in the flow of the flowable substance, for example the distribution of the magnetic compounds or more particularly to the distribution of ferromagnetic compounds present in the flow of the flowable substance, such as the distribution of steel fibres present in the flow of the flowable substance.

With distribution of additional material present in the flow of the flowable substance is meant the amount of additional material per unit of volume of the flow of the flowable substance.

The signal caused by the additional material present in the flow of the flowable substance is preferably measured in function of the time, for example in function of the time of unloading the flow of the flowable substance. The measurement is done on-line, meaning that the measurement is done during the flowing of the flow of flowable substance, for example during the unloading of the flow of the flowable substance. In a preferred embodiment the measurement is done on-line during the unloading of the flow of concrete from a mixing truck.

Once the volume flow Q in function of time is determined and the signal caused by the additional material present in the flow of the flowable substance is determined, the signal caused by the additional material present in the flow of the flowable substrate per unit of volume of the flow of the flowable substance can be determined by converting the measured signal caused by the additional material present in the flow of the flowable substance in a signal per unit of volume of the flow of the flowable substance.

If desired, the property of the flow of the flowable substance can be determined quantitatively by proportioning backwards the signal caused by the flow of the flowable substance.

The proportioning backwards can be done by using reference information. This reference information can for example be external information or information that is obtained from the flow of the flowable substance.

The external information is for example the total amount of additional material added to the flow of the flowable substance, for example the total amount of magnetic compounds or more particularly the total amount of ferromagnetic compounds such as steel fibres added to the flow of flowable substance.

The proportioning backwards can for example be done by a calibration using this reference information. A preferred way of proportioning backwards comprises a calibration using the total amount of additional material added to the flow of the flowable substance, for example the total amount of steel fibres added to the flow of the flowable substance.

The reference information that is obtained from the flow of the flowable substance is for example information obtained from markers added to the flow of the flowable substance. Preferably, the markers are indicative for the amount of additional material present in the flow of the flowable substance or indicative for the distribution of the additional material present in the flow of the flowable substance.

In case the markers are added proportional to the additional material present in the flow of the flowable substance, by detecting the markers the amount of additional material present in the flow of the flowable substance can be determined or can be verified.

This means that the detection of the markers can be used to proportion backwards the signal caused by the additional material present in the flow flow of the flowable substance to determine quantitatively the amount of additional material present in the flow of the flowable substance or to determine the distribution of additional material present in the flow of the flowable substance.

The markers added to the flow of the flowable substance are for example magnetic markers or RFID (Radio Frequency Identification) markers.

RFID or Radio Frequency Identification is an automatic identification method, relying on storing and remotely retrieving data using devices called RFID markers.

The term RFID marker means any RFID tag, transponder or any type of other marker transmitting a (predefined) message in response to a (predefined) received signal according to the RFID technology mentioned above.

The information stored on RFID markers can be configured in different ways: read-only, write-once-read many and read-write.

In one embodiment the RFID makers carry basic information that allow the detection of the marker as such, e.g. by sending out an "I am here" signal. In another embodiment, the RFID markers also carry other information either information related to the flow of the flowable substance, information related to the bulk material, for example related to the concrete or mortar, information related to the additional material added to the bulk material, for example related to the steel fibres added to the bulk material, such as the concrete.

Information relating to the steel fibres may for example include product identification, length L, diameter D, L/D, origin and type.

In case the flow of the flowable substance comprises metal fibres, RFID markers may be fixed or attached to one or more fibres, or they may be added separately from the fibres to the flow of the flowable substance. RFID markers may also be grouped together in a package and may be added as such to the flow of the flowable substance.

The method according to the present invention is in particular suitable to determine or monitor the amount of steel fibres present in a flow of concrete comprising steel fibre, i.e. to determine or monitor the amount of steel fibres per unit of volume of the flow of concrete during unloading of the flow of concrete. By this method the amount of steel fibres present per unit of volume of flow of concrete can be determined quantitatively, for example expressed as kilogram steel fibres per $m^3$ of concrete. Furthermore the method according to the present invention allows to determine deviations of the amount of fibres present in the flow of flowable substance during the unloading of the flow of concrete.

A preferred method to determine the amount of steel fibres present in a flow of concrete comprising steel fibres comprises the steps of providing a flow of concrete comprising steel fibres;

determining the volume flow of concrete comprising steel fibres at a detection point X along the flow of the flowable substance;

determining a signal caused by the steel fibres present in the flow of concrete comprising steel fibres at a detection point Y along the flow of the flowable substance. The signal that is determined is proportional to the amount of steel fibres present in the flow of concrete;

converting the signal caused by the steel fibres present in the flow of concrete in a signal per unit of volume of the flow of the flowable substance.

To obtain the amount of steel fibres per unit of volume of the flow of concrete comprising steel fibres, the above mentioned method comprises the additional step of proportioning backwards the signal caused by the steel fibres present in the flow of concrete per unit of volume of the flow of concrete comprising steel fibres to determine or monitor the amount of steel fibres present in the flow of concrete comprising steel fibres or to determine or monitor the distribution of steel fibres per unit of volume of the flow of concrete comprising steel fibres.

In this way the amount of steel fibres can be expressed quantitatively for example expressed in kg steel fibres per volume unit of concrete (=expressed in kg steel fibres/$m^3$ of flow of concrete comprising steel fibres).

In a preferred method the amount of steel fibres per unit of volume of the flow of concrete comprising steel fibres can be expressed as a deviation of the average amount of the steel fibres in the flow of concrete comprising steel fibres.

In a preferred method the proportioning backwards of the signal caused by the steel fibres present in the flow of concrete per unit of volume of the flow of concrete comprising steel fibres to determine or monitor the amount of steel fibres present in the flow of concrete comprising steel fibres or to determine or monitor the distribution of steel fibres per unit of volume of the flow of concrete comprising steel fibres is done by using external information, for example the total amount of steel fibres added to the total volume of the flow of the concrete comprising the steel fibres. In this case the proportioning backwards can be done by a calibration using the total amount of steel fibres added to the concrete as reference information.

In another preferred method the proportioning backwards of the signal caused by the steel fibres present in the flow of concrete per unit of volume of the flow of concrete comprising steel fibres to determine or monitor the amount of steel fibres present in the flow of concrete comprising steel fibres or to determine or monitor the distribution of steel fibres per unit of volume of the flow of concrete comprising steel fibres is done by using information obtained from markers added to the flow of concrete comprising steel fibres. The markers are preferably indicative of the amount of steel fibres present in the flow of concrete. The markers are for example RFID fibres. By detecting the markers, such as the RFID markers the amount of steel fibres present in the flow of concrete can be determined or monitored.

According to a second aspect of the present invention, an apparatus to determine or monitor the amount or the distribution of additional material present in a flow of a flowable substance is provided. The flow of the flowable substance comprises a bulk material and additional material.

The apparatus comprises a first device to determine the volume flow of the flow of the flowable substance;

a second device to determine a signal caused by the additional material present in the flow of the flowable substance;

tools to convert the signal measured by the second device in a signal per unit of volume of the flow of the flowable substance.

Possibly, the apparatus further comprises tools to proportion backwards the signal per unit of volume of the flow of the flowable substance to determine or monitor the amount of additional material present in the flow of the flowable substance or to determine or monitor the distribution of the additional material per unit of volume of the flow of the flowable substance.

The first device and the second device are located along the flow of the flowable substance. Preferably, the first and the second device are located below, above or around the flow of the flowable substance.

The first device and the second device may be located at the same or at different locations along the flow of the flowable substance.

The first device is for example determining the volume flow at detection point X or at a number of detection points $X_1, X_2, \ldots$.

The second device is for example determining the signal cause by the flow of the flowable substance at detection point Y or at a number of detection points $Y_1, Y_2, \ldots$.

In some embodiments the first and the second device can be integrated in one single device.

BRIEF DESCRIPTION OF FIGURES IN THE DRAWINGS

The invention will now be described into more detail with reference to the accompanying drawings whereby.

MODE(S) FOR CARRYING OUT THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Figure 1:
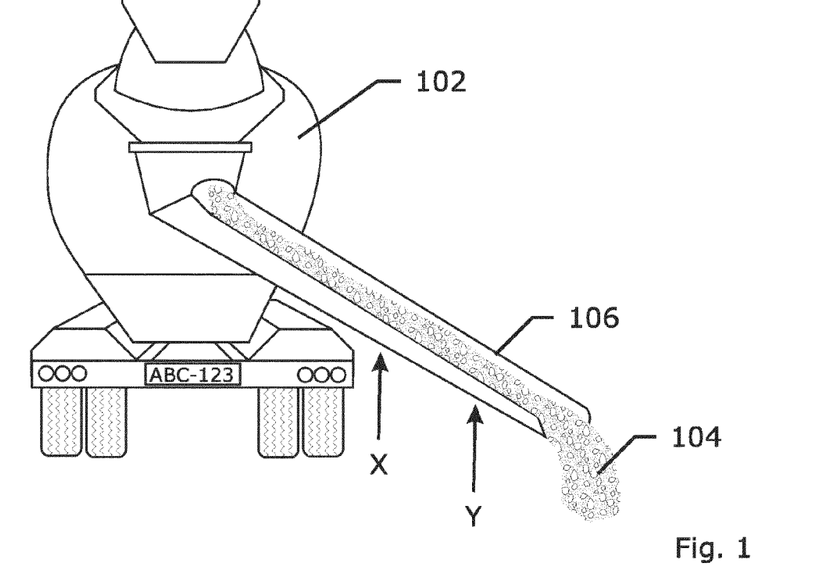
FIG. 1 is a schematic illustration of the unloading of a flow of concrete from a mixing truck.

A preferred method according to the present invention comprises a method to determine or monitor the amount of steel fibres present in a flow of concrete during unloading of the flow of concrete comprising steel fibres. The unloading of a mixing truck 102 is schematically shown in FIG. 1. Concrete comprising steel fibres is unloaded from a mixing truck 102 thereby providing a flow 104. While unloading, the flow 104 of concrete comprising steel fibres is flowing through a flow channel, for example an open flow channel such as a chute 106.

Figure 2:
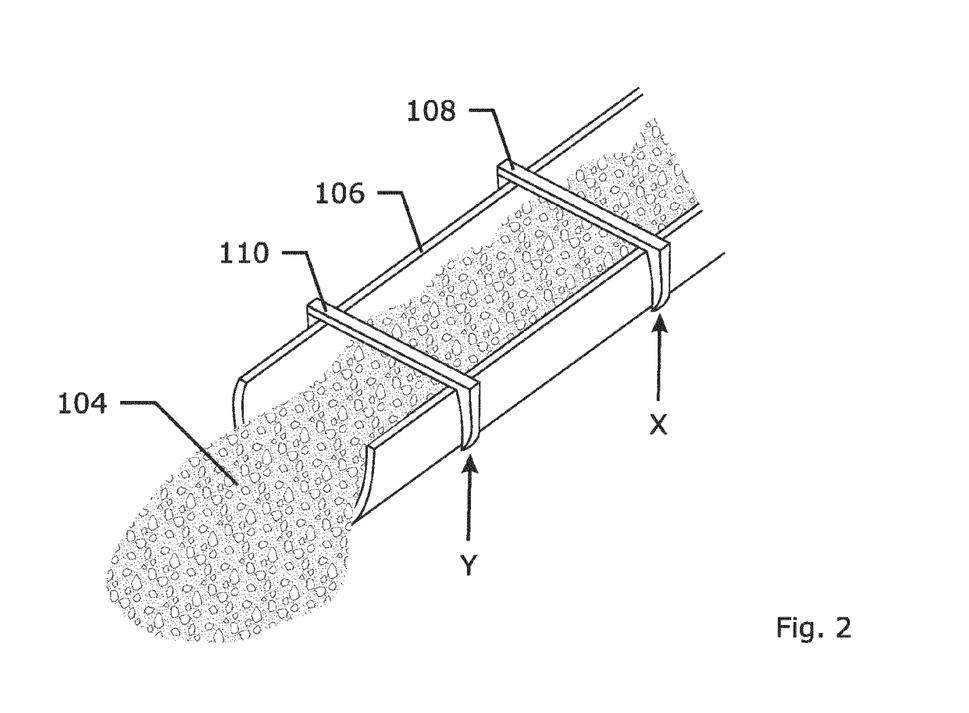
FIG. 2 is a schematic illustration of a chute of a mixing truck provided with an apparatus according to the present invention.

FIG. 2 shows a schematic illustration of a chute 106 of a mixing truck 102 provided with an apparatus according to the present invention.

The volume flow Q of the flow of concrete 104 comprising steel fibres is determined at one detection point or at a number of detection points located along the flow of concrete comprising steel fibres. The volume flow is for example determined at detection point X by device 108. The volume flow Q is determined by measuring the velocity of the flow 104 of concrete and the cross-sectional area of the concrete in the chute 106. In the embodiment shown in FIG. 2 the velocity of the flow 104 of concrete is determined by a device that is integrated in device 108. For a person skilled in the art, it is clear that the device 108 can be positioned at any point along the flow 104 of concrete.

The cross-sectional area of the concrete in the chute 106 can be calculated knowing the shape of the chute 106 and the height of the flow of concrete 104 in the chute 106. In the embodiment shown in FIG. 2 the height of the flow 104 of concrete is determined by a device that is for example integrated in device 108. For a person skilled in the art, it is clear that the height of the flow can be determined at any point along the flow 104 of the concrete. Preferably, the velocity of the flow and the height of the flow are determined at the same location along the flow of the flowable substance.

Once the velocity of the concrete and the cross-sectional area of the concrete are known, the volume flow Q can be calculated using the formula $$Q = v \cdot A$$

Figure 3:
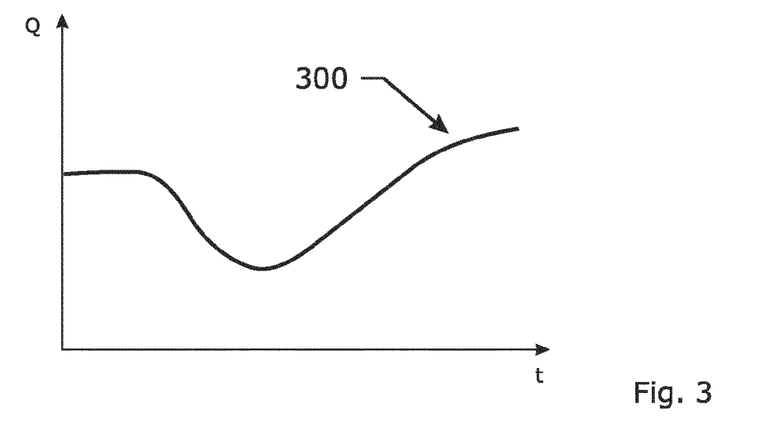
FIG. 3 is a schematic illustration of the measurement of the volume flow Q in function of time.

With v: the speed or velocity of the flow of the flowable substance;
A: the cross-sectional area FIG. 3 is a schematic representation of the volume flow Q (y-axis) measured at detection point X in function of time (x-axis), i.e. in function of the time of unloading the concrete comprising steel fibres.

The signal caused by the flow 104 of concrete comprising steel fibres is determined by device 110 for example at detection point Y. In the example shown in FIG. 1 and FIG. 2 the signal caused by the flow of concrete comprising the steel fibres is a magnetic signal caused by the steel fibres. The magnetic signal determined by device 110 is proportional to the amount of steel fibres present in the flow of concrete passing detection point Y.

Figure 4:
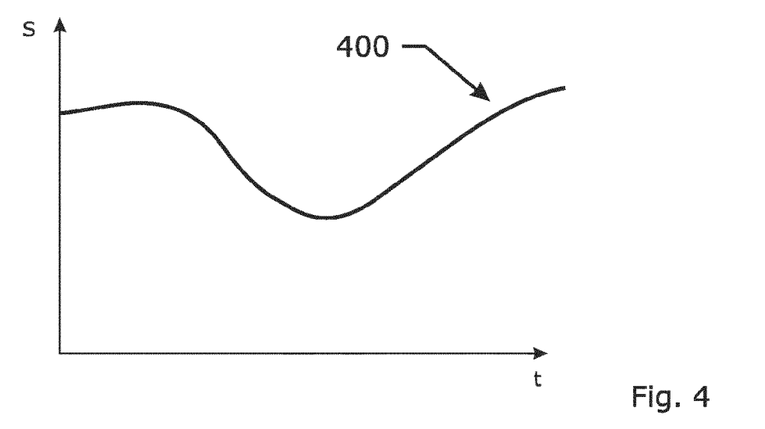
FIG. 4 is a schematic illustration of the measurement of the signal caused by the flow of a flowable substance in function of time.

The magnetic signal measured at detection point Y is measured in function of the time of unloading the concrete comprising the steel fibres. FIG. 4 is a schematic representation of the signal S (y-axis) detected at detection point Y measured in function of time (x-axis), i.e. in function of the time of unloading the concrete comprising steel fibres.

Once the volume flow Q in function of time is determined and the magnetic signal of the flow in function of time is measured, the magnetic signal caused by the flow per unit of volume of concrete comprising steel fibres that is unloaded can be calculated.

Figure 5:
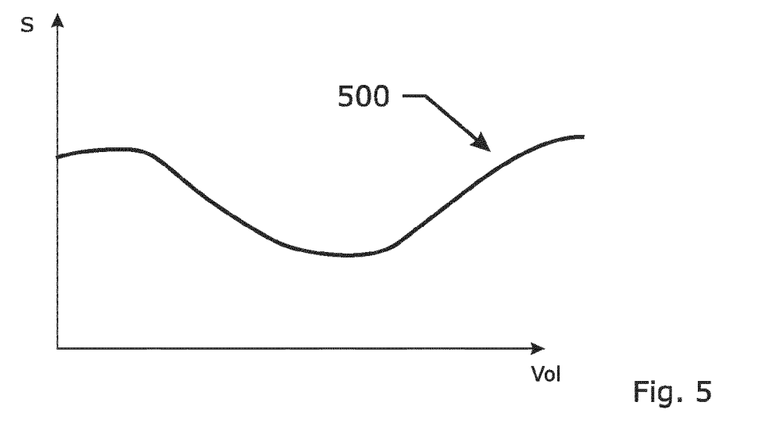
FIG. 5 is a schematic illustration of the signal caused by the flow of a flowable substance in function of volume of the flow of the flowable substance.

FIG. 5 is a schematic representation of the signal S (y-axis) detected in function of the volume of the flow of concrete comprising steel fibres. The magnetic signal caused by the flow per unit of volume of concrete comprising steel fibres is directly related to the amount of steel fibres present in the flow of concrete comprising steel fibres during unloading.

To determine the amount of steel fibres present in the flow of concrete comprising steel fibres during unloading of the flow the magnetic signal caused by the flow of concrete comprising steel fibres can be proportioned backwards using reference information. This reference information can for example be external information such as the total amount of steel fibres that is added to the concrete. By using a calibration method the magnetic signal per unit of volume of concrete comprising the steel fibres can be proportioned backwards to determine the amount of steel fibres in function of the volume of the flow of concrete comprising steel fibres.

In an alternative method, the reference information is obtained from markers added to the flow of concrete. The markers are for example RFID markers. The amount of RFID markers is for example proportional to the amount of steel fibres.

It is clear for a person skilled in the art that the RFID may also comprise additional information such as the type of steel fibres, the origin of the steel fibres, the method of manufacturing of the steel fibres, . . . .

FIGS. 6a, 6b, 6c and 6d are schematic illustrations of the amount of steel fibres present in the flow of concrete in function of the volume of the flow of the flowable substance.

Figure 6A:
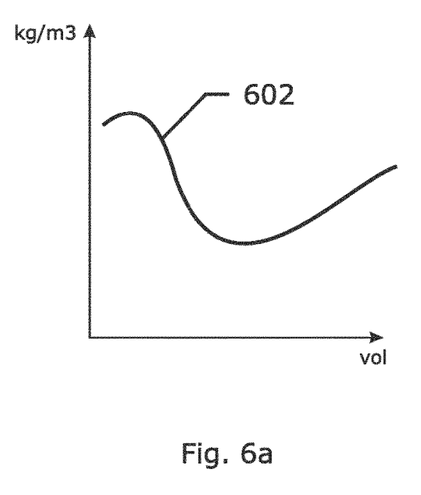
FIG. 6a, FIG. 6b, FIG. 6c and FIG. 6d are schematic illustrations of the amount of steel fibres caused by the flow of a flowable substance in function of the volume of the flow of the flowable substance.

In FIG. 6a curve 602 shows the amount of steel fibres (expressed in kg/m$^3$) in function of the absolute volume of the flow of concrete comprising steel fibres (expressed in m$^3$).

Figure 6B:
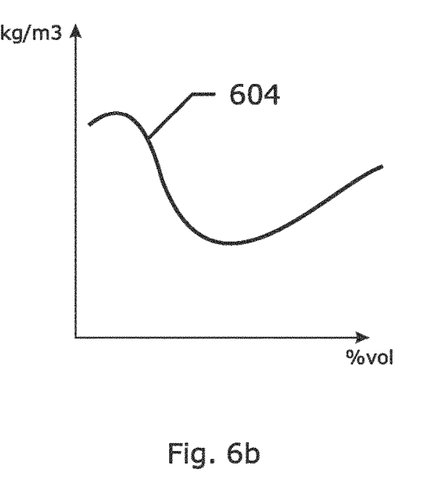

In FIG. 6b curve 604 shows the amount of steel fibres (expressed in kg/m$^3$) in function of the relative volume of the flow of concrete comprising steel fibres (expressed in % volume).

Figure 6C:
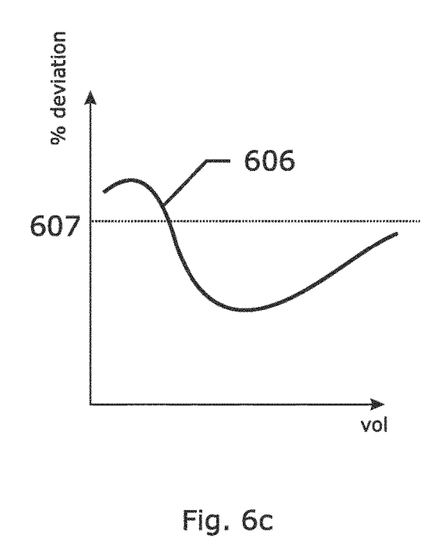

In FIG. 6c curve 606 shows the deviation of the amount of steel fibres from the average amount of steel fibres present during unloading of the flow of concrete comprising steel fibres in function of the absolute volume of the flow of concrete comprising steel fibres (expressed in m$^3$).

The deviation of the amount of steel fibres is expressed in percentage. The average amount of steel fibres is in FIG. 6c indicated with 607. Points of curve 606 that are situated above the line indicated with 607 show a positive deviation from the average amount of steel fibres, i.e. an amount of steel fibres above the average amount of steel fibres. Points of curve 606 that are situated below the line indicated with 607 show a negative deviation from the average amount of steel fibres, i.e. an amount of steel fibres below the average amount of steel fibres.

Figure 6D:
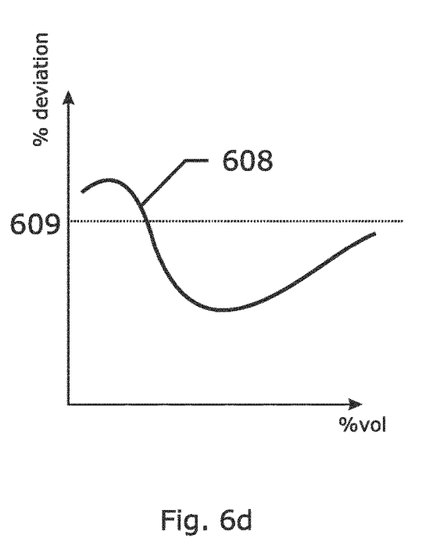

In FIG. 6d curve 608 shows the deviation of the amount of steel fibres from the average amount of steel fibres present during unloading of the flow of concrete comprising steel fibres in function in function of the relative volume of the flow of concrete comprising steel fibres (expressed in % volume).

The deviation of the amount of steel fibres is expressed in percentage. The average amount of steel fibres is in FIG. 6d indicated with 609. Points of curve 608 that are situated above the line indicated with 609 show a positive deviation from the average amount of steel fibres, i.e. an amount of steel fibres above the average amount of steel fibres. Points of curve 608 that are situated below the line indicated with 607 show a negative deviation from the average amount of steel fibres, i.e. an amount of steel fibres below the average amount of steel fibres.

The invention claimed is:

1. A method to determine or monitor the amount or distribution of additional material present in a flow of a flowable substance, said method comprising the steps of
   providing a flow of a flowable substance in an open channel, said flow of said flowable substance comprising bulk material comprising concrete or mortar and additional material comprising magnetic material;
   determining the volume flow of said flow of said flowable substance at one or more detection points X along said flow of said flowable substance;
   determining a signal caused by said additional material present in said flow of said flowable substance at one or more detection points Y along said flow of said flowable substance, said signal being proportional to inductance or magnetic properties, the inductance or magnetic properties being proportional to the amount of said additional material present in said flow of said flowable substance passing said one or more detection points Y, said one or more detection points Y being the same as or different from said one or more detection points X;
   converting said signal caused by said additional material present in said flow of said flowable substance into a signal per unit of volume of said flow of said flowable substance.

2. A method according to claim 1, wherein said method comprises the additional step of
   proportioning backwards said signal per unit of volume of said flow of said flowable substance to determine or monitor the amount of said additional material present in said flow of said flowable substance or to determine or monitor the distribution of said additional material present in said flow of said flowable substance.

3. A method according to claim 2, wherein said proportioning backwards is done by using reference information, said reference information being external information or information that is obtained from the flow of flowable substance.

4. A method according to claim 3, wherein said reference information is external information.

5. A method according to claim 3, wherein said reference information is obtained from markers added to said flow of said flowable substance, said markers being indicative for the amount of additional material present in said flow of said flowable substance.

6. A method according to claim 5, wherein said markers are magnetic markers or RFID markers.

7. A method according to claim 1, wherein said magnetic material comprises material selected from the group consisting of metal particles, metal components, particles or components comprising metal and any combination thereof.

8. A method according to claim 1, wherein said magnetic material comprises metal fibres.

9. A method according to claim 1, wherein said volume flow and said signal caused by additional material present in said flow of said flowable substance are determined at the same location.

10. A method according to claim 1, wherein said volume flow and said signal caused by said additional material present in said flow of said flowable substance are determined at different locations.

11. An apparatus to determine or monitor the amount or the distribution of additional material present in a flow of a flowable substance in an open channel, said flow of said flowable substance comprising a bulk material comprising concrete or mortar and additional material comprising magnetic material, said apparatus comprising
   a first device to determine the volume flow of said flow of said flowable substance in said open channel;
   a second device to measure a signal caused by a magnetic property or an inductance of said additional material present in said flow of said flowable substance;
   tools to convert the signal measured by said second device into a signal per unit of volume of said flow of said flowable substance.

12. An apparatus according to claim 11, further comprising tools to proportion backwards said signal per unit of volume of said flow of said flowable substance to determine or monitor the amount of additional material present in said flow of said flowable substance or to determine the distribution of the additional material per unit of volume of said flow of said flowable substance.

* * * * *